US012666129B2

(12) United States Patent
Abbas

(10) Patent No.: US 12,666,129 B2
(45) Date of Patent: Jun. 23, 2026

(54) CAMERA PRIVACY FOR TELEMEDICINE

(71) Applicant: Vitalchat, Inc., Ashburn, VA (US)

(72) Inventor: Ghafran Abbas, Ashburn, VA (US)

(73) Assignee: Vitalchat, Inc., Ashburn, VA (US)

( * ) Notice: Subject to any disclaimer, the term of this patent is extended or adjusted under 35 U.S.C. 154(b) by 77 days.

(21) Appl. No.: 18/626,806

(22) Filed: Apr. 4, 2024

(65) Prior Publication Data

US 2025/0317640 A1 Oct. 9, 2025

(51) Int. Cl.
| | |
|---|---|
| *H04N 23/57* | (2023.01) |
| *G03B 11/04* | (2021.01) |
| *G16H 40/67* | (2018.01) |
| *H04N 23/55* | (2023.01) |
| *H04N 23/667* | (2023.01) |

(52) U.S. Cl.
CPC ........... *H04N 23/57* (2023.01); *G03B 11/043* (2013.01); *G16H 40/67* (2018.01); *H04N 23/55* (2023.01); *H04N 23/667* (2023.01)

(58) Field of Classification Search
CPC ...... H04N 23/55; H04N 23/57; H04N 23/667; G03B 11/04; G03B 11/041; G03B 11/043; G16H 40/60; G16H 40/63; G16H 40/67; G06F 21/70; G06F 21/82; G06F 21/83
See application file for complete search history.

(56) References Cited

U.S. PATENT DOCUMENTS

| | | | |
|---|---|---|---|
| 8,751,531 | B2 | 6/2014 | Ishikawa et al. |
| 9,244,906 | B2 | 1/2016 | Houache |
| 10,165,945 | B1 | 1/2019 | Suarez Saiz et al. |
| 2009/0243833 | A1 | 10/2009 | Huang et al. |
| 2015/0213414 | A1 | 7/2015 | Zuckerman et al. |
| 2017/0287316 | A1 | 10/2017 | Wildman et al. |
| 2019/0281161 | A1 | 9/2019 | Yamakawa |
| 2019/0281200 | A1* | 9/2019 | Files ...................... H04N 7/142 |
| 2020/0258619 | A1 | 8/2020 | Ogawa |
| 2020/0258649 | A1 | 8/2020 | Yuan et al. |
| 2022/0197110 | A1* | 6/2022 | Li .......................... G06F 1/3287 |
| 2023/0043837 | A1* | 2/2023 | Files ...................... H04N 23/55 |
| 2024/0028780 | A1* | 1/2024 | Perez ...................... G06F 21/32 |

* cited by examiner

*Primary Examiner* — Daniel M Pasiewicz

(74) *Attorney, Agent, or Firm* — Young Basile Hanlon & MacFarlane, P.C.

(57) ABSTRACT

A system of camera privacy for telemedicine includes a computing device, a camera comprising a lens, and a cover extending over at least the lens. The cover is communicatively connected to the computing device, and the cover is configurable to be in a first state or a second state. The first state configures the cover to block a field of view of the lens to prevent the camera from capturing visual information from a far side of the cover. The computing device is configured to identify a first condition. In response to identifying the first condition, the computing device transmits a signal to the cover that configures the cover to be in the second state.

20 Claims, 7 Drawing Sheets

200

300

301    320    302

Figure 5:
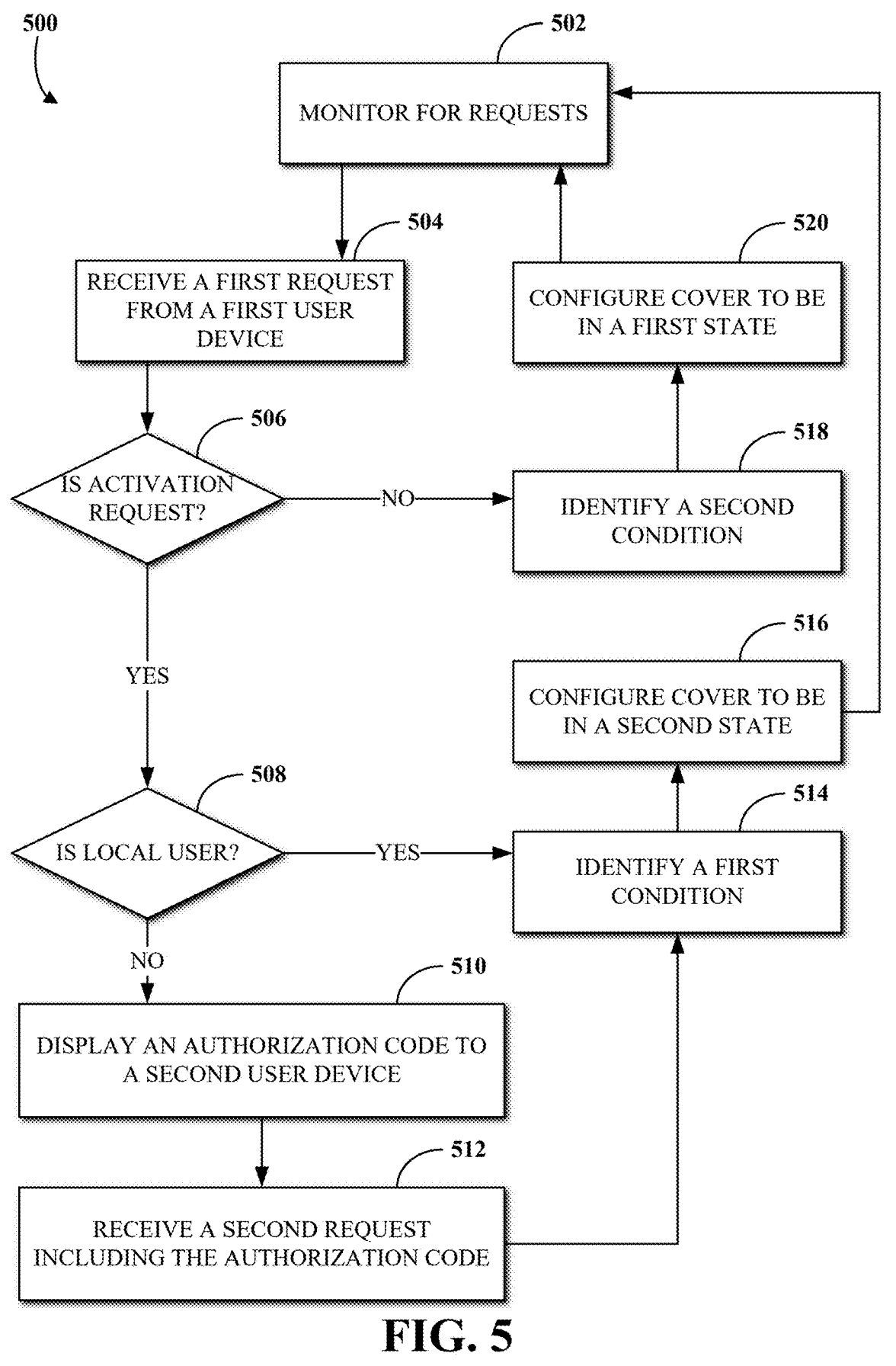

500

502

MONITOR FOR REQUESTS

504

RECEIVE A FIRST REQUEST FROM A FIRST USER DEVICE

506

IS ACTIVATION REQUEST?

NO

520

CONFIGURE COVER TO BE IN A FIRST STATE

518

IDENTIFY A SECOND CONDITION

YES

516

CONFIGURE COVER TO BE IN A SECOND STATE

508

IS LOCAL USER?

YES

514

IDENTIFY A FIRST CONDITION

NO

510

DISPLAY AN AUTHORIZATION CODE TO A SECOND USER DEVICE

512

RECEIVE A SECOND REQUEST INCLUDING THE AUTHORIZATION CODE

604 LOCAL USER

608 MONITORING DEVICE

606 USER DEVICE

602 REMOTE USER

OPEN AUDIO 613

GENERATE CODE 616

612 CALL REQUEST

614 SOUND RESPONSE

618 READ CODE

620 ENTER CODE

622 VIDEO ENABLED

610 REMOTE USER INITIATES A CALL

700

800

900
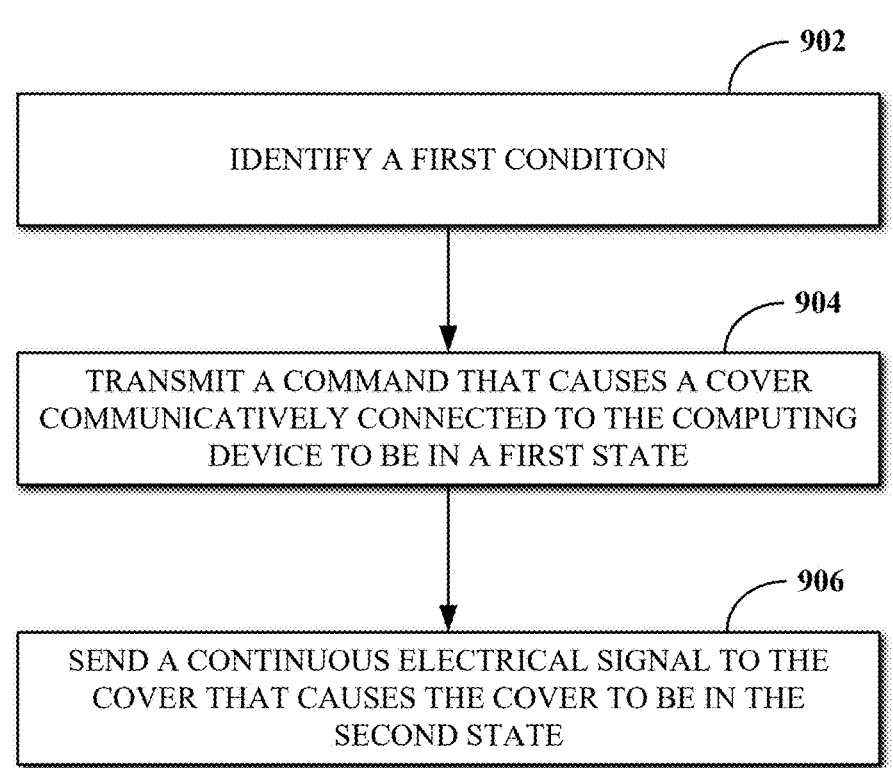
902
IDENTIFY A FIRST CONDITON
904
TRANSMIT A COMMAND THAT CAUSES A COVER
COMMUNICATIVELY CONNECTED TO THE COMPUTING
DEVICE TO BE IN A FIRST STATE
906
SEND A CONTINUOUS ELECTRICAL SIGNAL TO THE
COVER THAT CAUSES THE COVER TO BE IN THE
SECOND STATE
FIG. 9

CAMERA PRIVACY FOR TELEMEDICINE

TECHNICAL FIELD

This disclosure relates generally to telemedicine and more specifically to camera privacy in telemedicine.

SUMMARY

Disclosed herein are implementations of door-knocking for teleconferencing.

A first aspect is a system including a computing device, a camera comprising a lens, and a cover extending over at least the lens. The cover is communicatively connected to the computing device, and the cover is configurable to be in a first state or a second state. The first state configures the cover to block a field of view of the lens to prevent the camera from capturing visual information from a far side of the cover. The computing device is configured to identify a first condition. In response to identifying the first condition, the computing device transmits a signal to the cover that configures the cover to be in the second state.

A second aspect is a method for camera privacy, the method includes identifying a first condition by a computing device. In response to identifying the first condition, transmitting, by the computing device, a command that causes a cover communicatively connected to the computing device to be in a first state, wherein the cover extends over at least a lens of a camera, wherein the cover is configurable to be in the first state or a second state, wherein the first state configures the cover to block a field of view of the lens from capturing visual information from a far side of the cover.

A third aspect is a computer-readable medium for camera privacy. The computer-readable medium stores instructions operable to cause a processor of a computing device to perform operations including identifying a first condition by the computing device. In response to identifying the first condition, transmitting, by the computing device, a command that causes a cover communicatively connected to the computing device to be in a first state. The cover extends over at least a lens of a camera. The cover is configurable to be in the first state or a second state. The first state configures the cover to block a field of view of the lens from capturing visual information from a far side of the cover.

These and other aspects of the present disclosure are disclosed in the following detailed description of the embodiments, the appended claims, and the accompanying figures.

It will be appreciated that aspects can be implemented in any convenient form. For example, aspects may be implemented by appropriate computer programs which may be carried on appropriate carrier media which may be tangible carrier media (e.g., disks) or intangible carrier media (e.g., communications signals). Aspects may also be implemented using suitable apparatus which may take the form of programmable computers running computer programs arranged to implement the methods and/or techniques disclosed herein. Aspects can be combined such that features described in the context of one aspect may be implemented in another aspect.

BRIEF DESCRIPTION OF THE DRAWINGS

The disclosure is best understood from the following detailed description when read in conjunction with the accompanying drawings.

FIG. 5 is an example of a flowchart of a technique for teleconferencing between a monitoring device and a user device where camera privacy for telemedicine can be used according to implementations of this disclosure.

FIG. 9 is an example of a flowchart of a technique for activating and deactivating camera privacy measures for telemedicine according to implementations of this disclosure.

Figure 1:
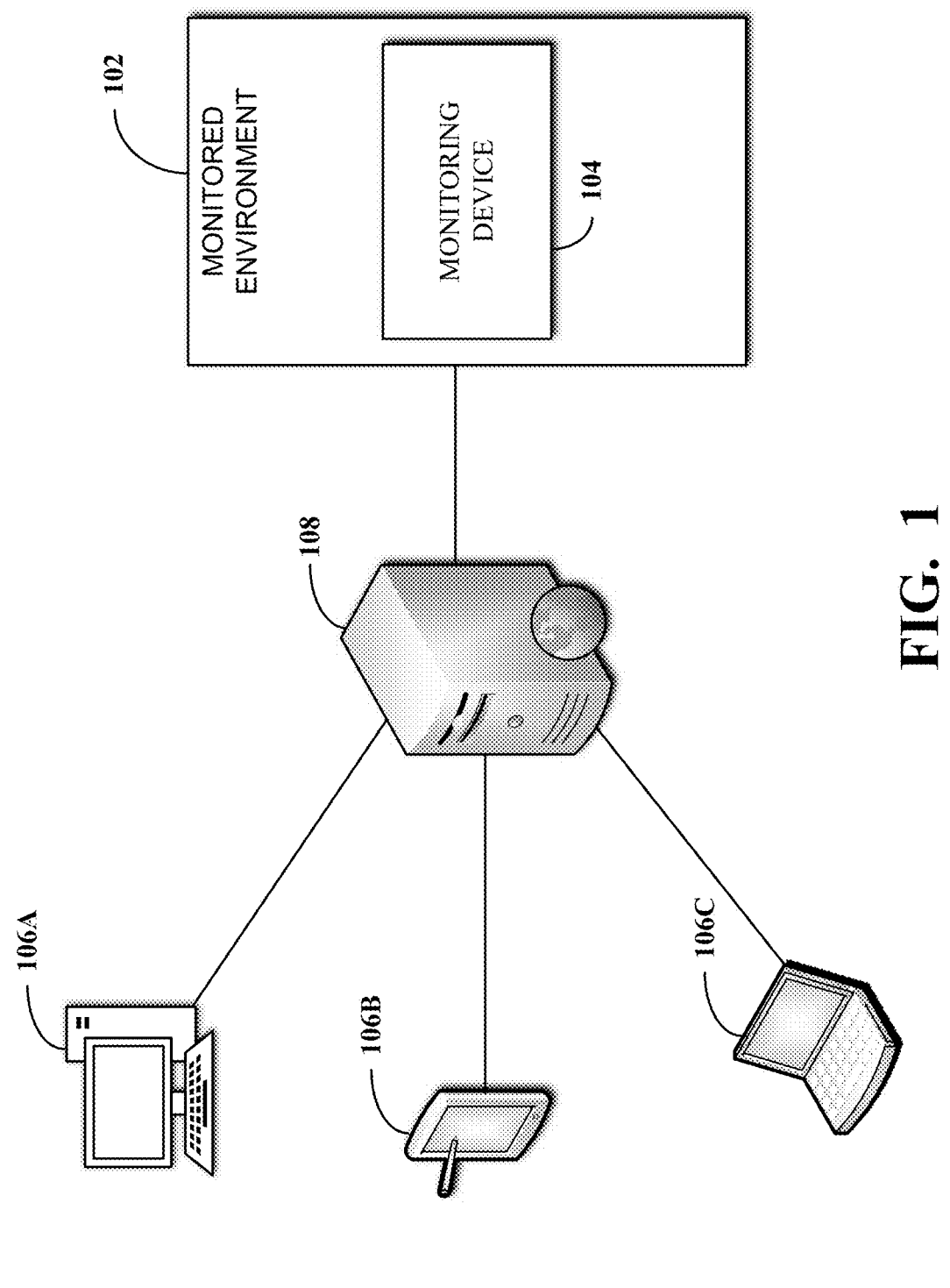
FIG. 1 is a schematic of an example of a system according to implementations of this disclosure.

These and other aspects of the present disclosure are disclosed in the following detailed description of the embodiments, the appended claims, and the accompanying figures.

It will be appreciated that aspects can be implemented in any convenient form. For example, aspects may be implemented by appropriate computer programs which may be carried on appropriate carrier media which may be tangible carrier media (e.g., disks) or intangible carrier media (e.g., communications signals). Aspects may also be implemented using a suitable apparatus, which may take the form of programmable computers running computer programs arranged to implement the methods and/or techniques disclosed herein. Aspects can be combined such that features described in the context of one aspect may be implemented in another aspect.

DETAILED DESCRIPTION

The use of telehealth, telemedicine, telemonitoring (remotely monitoring different aspects of a patient and/or a patient's room), and/or televisits (collectively, and for brevity, telemedicine) offers substantial benefits, connecting patients with healthcare providers remotely. "Tele" in this context means "from a distance" or "remotely," and more specifically using telecommunication capabilities. The room of a patient may be equipped (in a fixed or in a movable way) with a telecommunication device (e.g., a monitoring device) that enables telemedicine. The telecommunication device may enable audio and/or visual communication between a remote user (e.g., a physician, a family member, a person initiating a call, etc.) and a local user (e.g., the patient, a nurse, a person receiving the call, etc.) who is in the room.

A telemedicine visit may begin based on a scheduled visit in which the remote user and the local user agreed to meet remotely at a specified time. A telemedicine visit may begin with a remote user (such as a physician) sending a request to activate the telecommunication device within the local user's room. Alternatively, a telemedicine visit may begin at a regularly scheduled time based on a patient monitoring requirement and/or need. During the telemedicine visit audio and/or visual communication may be utilized. In particular, the visual communication may be accomplished via a camera attached or otherwise connected to the telecommunication device. The presence of a camera within the room may raise privacy or security concerns for the local user.

Ensuring local user privacy and establishing trust poses a significant challenge in telemedicine. Traditional ways for addressing local user privacy are limited, especially in the context of camera privacy. Manual camera adjustments, such as reorienting the angle of the camera or covering the camera with a physical cover can be easily overlooked, necessitating frequent local user intervention.

Fixed cameras, characterized by fixed points of view without the flexibility to be repositioned, may lack mechanisms (e.g., a cover) for obscuring the lens. The lack of a cover can elevate privacy concerns for local users, especially the patients. While a local user, in some instances, may be able to manually cover the lens, this solution is contingent on the camera being within easy reach of the local user and that the local user is physically and safely capable of reaching the camera. In many instances, the camera may be located in a hard-to-reach or otherwise inaccessible location further complicating privacy protection efforts.

Motorized cameras (e.g., those equipped with pan-tilt-zoom (PTZ) functionality) offer the capability to adjust their positioning remotely, allowing for dynamic changes in the camera's field of view. Despite this adaptability, motorized cameras may not always provide a viable solution for scenarios demanding an expansive field of view. The movement range of a PTZ camera might be insufficient to entirely exclude the local user from the camera's field of vision. Moreover, altering the camera's orientation to modify the field of view could necessitate manual intervention by the local user, echoing the limitations encountered with fixed cameras. Additionally, reorienting the camera for privacy reasons necessitates resetting it to its original, correct position for each telemedicine session, adding another layer of complexity to its use.

Implementations of camera privacy for telemedicine according to this disclosure enable privacy in telemedicine. Some embodiments employ an electronically controlled physical or smart glass cover to obscure at least a portion of a camera (e.g., the whole of the camera or at least the lens of the camera) placed in a local user's room. The at least the portion of the camera can be obscured on demand or in response to identified (e.g., detected) conditions. The cover can be manually controlled (such as by a local user) and can be automatically controlled, such as by a monitoring device that activates or deactivates the cover based on identified conditions, such as, but not limited to, scheduling or initiating/concluding telemedicine sessions.

In some implementation, a system comprises a computing device, a camera including a lens, and a cover extending over at least the lens. The cover is communicatively connected to the computing device, and the cover is configurable to be in a first state or a second state. The first state configures the cover to block a field of view of the lens to prevent the camera from capturing visual information from a far side of the cover. The computing device is configured to identify a first condition. In response to identifying the first condition, the computing device is configured to transmit a signal to the cover that configures the cover to be in the second state.

Details of camera privacy for telehealth are described herein with initial reference to a system in which the teachings herein can be implemented.

FIG. 1 is an schematic of an example of a system 100 according to implementations of this disclosure. The system 100 includes a monitored environment 102, a monitoring device 104, a user device 106 (e.g., one of the devices 106A through 106C), and a server 108.

The monitored environment 102 can be a patient hospital room, a nursing home room, a room of a home patient, a manufacturing line, a workstation, a laboratory, and the like. The monitored environment 102 includes and/or can be viewed using the monitoring device 104. The monitored environment 102 can be remotely monitored from the user device 106. The user device 106 can be one or more of a desktop computer 106A, a mobile device 106B (such as tablet, a smart phone, and the like), a laptop computer 106C, or some other device that can be used to access, communicate with, and/or control (directly or indirectly) the monitoring device 104. A user (not shown) of the user device 106 can monitor the monitored environment 102 via the monitoring device 104. That the monitored environment 102 is remotely monitored by the user means that the user may not physically be in the monitored environment 102 while performing the monitoring.

In the case that the monitored environment 102 is a patient hospital room, the user can be a physician, a nurse, another health-care practitioner, a family member of the patient, and/or the like. For example, the physician may be remotely responding to (e.g., diagnosing, mitigating, assessing, etc.) a patient emergency or remotely performing patient rounds. The nurse may be monitoring patients, including the monitored environment 102 from a nurses station to, for example, ensure that no patient is falling, is in need of help, is distressed, and/or the like. The family member of the patient may remotely visit with the patient using the monitoring device 104.

The monitoring device 104 can be configured to and/or used to capture video, images, audio, environmental conditions, or other characteristics of the monitored environment. The characteristics of the monitored environment can be transmitted to one or more users of the user devices 106. Via the user device 106, the user can interact with the monitoring device, such as by sending and/or receiving captured video and/or audio, sending commands to the monitoring device 104, and the like.

The user device 106 and the monitoring device 104 can communicate via the server 108. For example, the user device 106 can send commands to the server 108, which relays the command to the monitoring device. Similarly, the monitoring device 104 can send information to the server 108, which relays the information to the user device 106.

To illustrate, the monitoring device 104 can include a camera that is configured to view the monitored environment 102. The user device 106 can issue a request to the server 108 to establish a connection with the monitoring device 104. The server 108 can establish the connection. Issuing a request to the server 108 to establish a connection can include, for example, the user device 106 connecting to a patient by the patient's room number or name; the server 108 determining the monitoring device 104 of the patient (i.e., the monitoring device that is in the patient's room); and the server 108 connecting the user device 106 and the monitoring device 104. The connection session may be an video communication session during which the user can communicate visually and/or verbally with a person in the patient's room. The user device 106, may during the connection session, send a pan, tilt, or zoom (PTZ) command to the camera of the monitoring device 104 via the server 108. The monitoring device 104 can update the view of the monitored environment according to the PTZ command and send back, via the server 108, a video and/or image of the updated view of the monitored environment, which can then be displayed on a display of the user device 106. In an example, the server 108 can allow certain users to control monitoring device and not allowing other user devices to control the monitoring device.

In another example (not shown), the user device 106 can establish a peer-to-peer communication channel with the monitoring device 104. For example, in response to the connection request, the server 108 can facilitate the establishment of the peer-to-peer (e.g., direct) communication between the user device 106 and the monitoring device 104.

The server 108 can be deployed (e.g., physically located) on premise at the location of the monitored environment. The server 108 can be deployed on a same local area network (LAN) of the monitoring device 104. The server 108 can be deployed on a same wide area network (WAN) of the monitoring device 104. The server 108 can be a cloud-based server. Other deployments of the server 108 are possible.

The monitoring device 104, the user device 106, and the server 108 can communicate over any suitable network. The network (not shown) can be, for example, the Internet or an Internet Protocol (IP) network, such as the World Wide Web. The network can be a LAN, a WAN, a virtual private network (VPN), cellular telephone network, a private network, an extranet, an intranet, any other means of transferring information (e.g., video streams, audio streams, images, other information), or a combination thereof from one end point to another end point.

In an example, the user device 106 and the monitoring device 104 may communicate using a real-time transport protocol (RTP) for transmission of the media content, which may be encoded, over the network. In another implementation, a transport protocol other than RTP may be used (e.g., a Hypertext Transfer Protocol-based (HTTP-based) streaming protocol). For example, the user device 106 can transmit and/or receive media content (e.g., audio and/or video content) to and/or from the monitoring device 104 via WebRTC, which provides web browsers and mobile applications with real-time communication. However, the disclosure herein is not so limited and any other real-time transmission protocol can be used.

Figure 2:
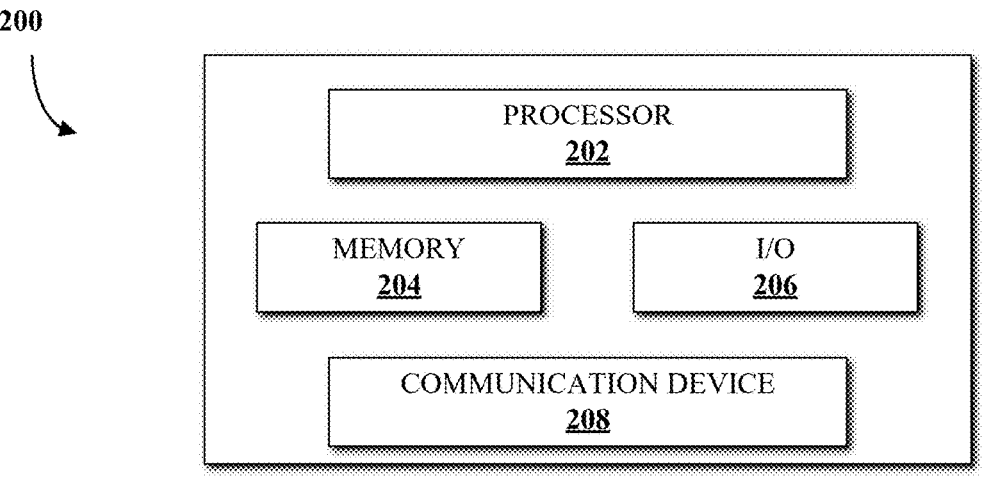
FIG. 2 is a block diagram of an example of a computing device.

FIG. 2 is a block diagram of an example of a computing device 200. Each of the monitoring device 104, the user device 106, or the server 108 can be implemented, at least partially, by the computing device 200.

The computing device 200 can be implemented by any configuration of one or more computers, such as a micro-computer, a mainframe computer, a supercomputer, a general-purpose computer, a special-purpose/dedicated computer, an integrated computer, a database computer, a remote server computer, a personal computer, a laptop computer, a tablet computer, a cell phone, a personal data assistant (PDA), a wearable computing device, or a computing service provided by a computing service provider, for example, a web host or a cloud service provider. In some implementations, the computing device can be implemented in the form of multiple groups of computers that are at different geographic locations and can communicate with one another, such as by way of a network. While certain operations can be shared by multiple computers, in some implementations, different computers are assigned to different operations. In some implementations, the system 100 can be implemented using general-purpose computers/processors with a computer program that, when executed, carries out any of the respective methods, algorithms, and/or instructions described herein. In addition, or alternatively, for example, special-purpose computers/processors including specialized hardware can be utilized for carrying out any of the methods, algorithms, or instructions described herein.

The computing device 200 can have an internal configuration of hardware including a processor 202 and a memory 204. The processor 202 can be any type of device or devices capable of manipulating or processing information. In some implementations, the processor 202 can include a central processor (e.g., a central processing unit or CPU). In some implementations, the processor 202 can include a graphics processor (e.g., a graphics processing unit or GPU). Although the examples herein can be practiced with a single processor as shown, advantages in speed and efficiency can be achieved by using more than one processor. For example, the processor 202 can be distributed across multiple machines or devices (each machine or device having one or more processors) that can be coupled directly or connected via a network (e.g., a local area network). The memory 204 can include any transitory or non-transitory device or devices capable of storing executable codes and data that can be accessed by the processor (e.g., via a bus). The memory 204 herein can be a random-access memory (RAM) device, a read-only memory (ROM) device, an optical/magnetic disc, a hard drive, a solid-state drive, a flash drive, a security digital (SD) card, a memory stick, a compact flash (CF) card, or any combination of any suitable type of storage device. In some implementations, the memory 204 can be distributed across multiple machines or devices, such as in the case of a network-based memory or cloud-based memory. The memory 204 can include data (not shown), an operating system (not shown), and an application (not shown). The data can include any data for processing (e.g., an audio stream, a video stream, a multimedia stream, user commands, and/or other data). The application can include programs that permit the processor 202 to implement instructions to generate control signals for performing functions of the techniques in the following description.

In some implementations, in addition to the processor 202 and the memory 204, the computing device 200 can also include a secondary (e.g., external) storage device (not shown). When present, the secondary storage device can provide additional memory when high processing needs exist. The secondary storage device can be a storage device in the form of any suitable non-transitory computer-readable medium, such as a memory card, a hard disk drive, a solid-state drive, a flash drive, or an optical drive. Further, the secondary storage device can be a component of the computing device 200 or can be a shared device accessible via a network. In some implementations, the application in the memory 204 can be stored in whole or in part in the secondary storage device and loaded into the memory 204 as needed for processing.

In addition to the processor 202 and the memory 204, the computing device 200 can include input/output (I/O) devices. For example, the computing device 200 can include an I/O device 206. The I/O device 206 can be implemented in various ways, for example, it can be a display that can be coupled to the computing device 200 and configured to display a rendering of graphics data. The I/O device 206 can be any device capable of transmitting a visual, acoustic, or tactile signal to a user, such as a display, a touch-sensitive device (e.g., a touchscreen), a speaker, an earphone, a light-emitting diode (LED) indicator, or a vibration motor. The I/O device 206 can also be any type of input device either requiring or not requiring user intervention, such as a keyboard, a numerical keypad, a mouse, a trackball, a microphone, a touch-sensitive device (e.g., a touchscreen), a sensor, or a gesture-sensitive input device. If the I/O device 206 is a display, for example, it can be a liquid crystal display (LCD), a cathode-ray tube (CRT), or any other output device capable of providing a visual output to an individual. In some cases, an output device can also function as an input device. For example, the output device can be a touchscreen display configured to receive touch-based input.

The I/O device 206 can alternatively or additionally be formed of a communication device for transmitting signals and/or data. For example, the I/O device 206 can include a wired means for transmitting signals or data from the computing device 200 to another device. For another example, the I/O device 206 can include a wireless transmitter or receiver using a protocol compatible to transmit signals from the computing device 200 to another device or to receive signals from another device to the computing device 200.

In addition to the processor 202 and the memory 204, the computing device 200 can optionally include a communication device 208 to communicate with another device. Optionally, the communication can be via a network. The network can be one or more communications networks of any suitable type in any combination, including, but not limited to, networks using Bluetooth communications, infrared communications, near-field communications (NFCs), wireless networks, wired networks, local area networks (LANs), wide area networks (WANs), virtual private networks (VPNs), cellular data networks, or the Internet. The communication device 208 can be implemented in various ways, such as a transponder/transceiver device, a modem, a router, a gateway, a circuit, a chip, a wired network adapter, a wireless network adapter, a Bluetooth adapter, an infrared adapter, an NFC adapter, a cellular network chip, or any suitable type of device in any combination that is coupled to the computing device 200 to provide functions of communication with the network.

The computing device 200 can also include or be in communication with an image-sensing device (not shown), for example a camera, or any other image-sensing device now existing or hereafter developed that can sense an image such as the image of a user operating the computing device 200 or a view of a monitored environment. The image-sensing device can be positioned such that it is directed to capture a view of the monitored environment. For example, the image-sensing device can be directed toward a patient and/or a patient bed in a hospital room. In an example, the position and optical axis of the image-sensing device can be configured and/or controlled such that the field of vision (i.e., the view) includes an area of interest.

The computing device 200 can also include or be in communication with a sound-sensing device, for example a microphone, or any other sound-sensing device now existing or hereafter developed that can sense sounds near the computing device 200. The sound-sensing device can be positioned or controlled to be positioned such that it is directed toward a monitored environment so as to capture speech, other utterances, or other sounds within the monitored environment. The sound-sensing device can be configured to receive sounds, for example, speech or other utterances made by the user while the user operates the computing device 200. The computing device 200 can also include or be in communication with a sound playing device.

The computing device 200 (and any algorithms, methods, instructions, etc., stored thereon and/or executed thereby) can be realized in hardware including, for example, intellectual property (IP) cores, application-specific integrated circuits (ASICs), programmable logic arrays, optical processors, programmable logic controllers, microcode, firmware, microcontrollers, servers, microprocessors, digital signal processors, or any other suitable circuit. In this disclosure, the term "processor" should be understood as encompassing any the foregoing, either singly or in combination. The terms "signal," "data," and "information" are used interchangeably.

Figure 3:
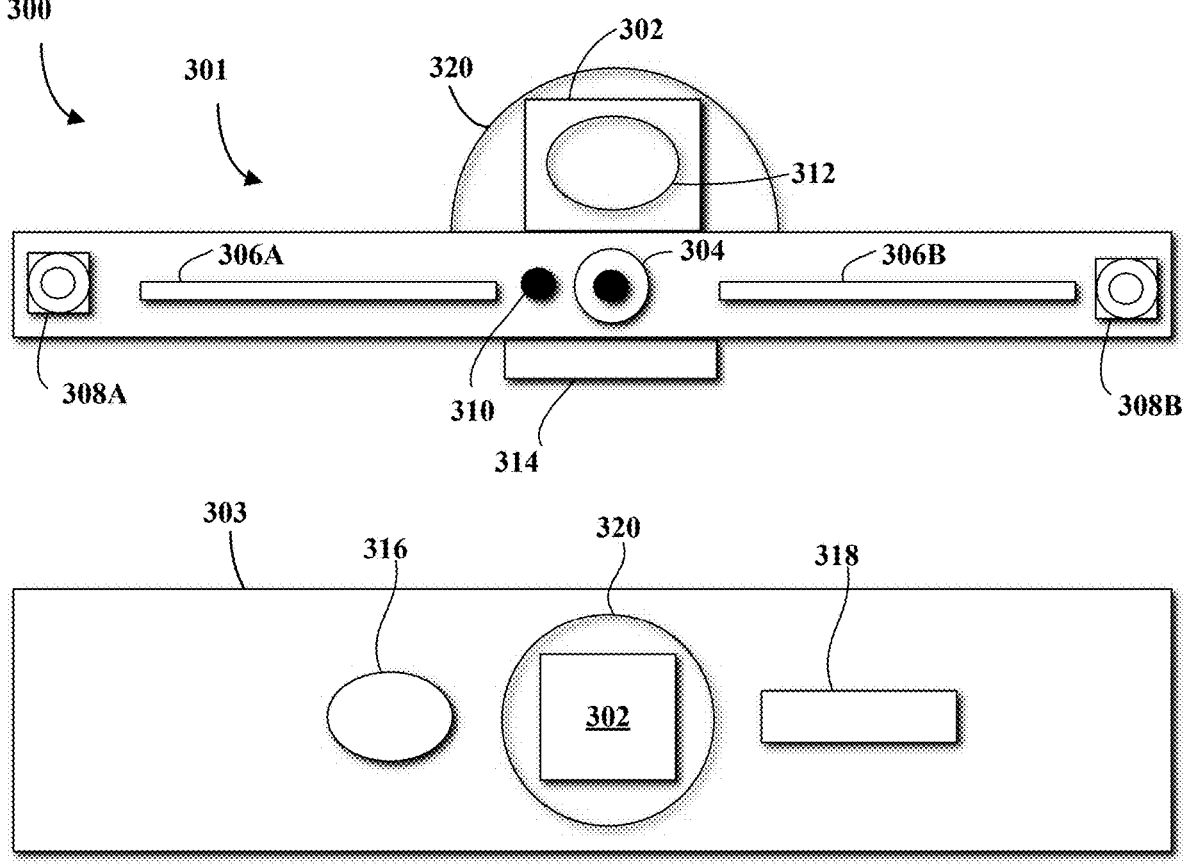
FIG. 3 is a block diagram of an example of a monitoring device according to implementations of this disclosure.

FIG. 3 is a block diagram of an example of a monitoring device 300 according to implementations of this disclosure. The monitoring device 300 can be the monitoring device 104 of FIG. 1. FIG. 3 shows a front view 301 and a top view 303 of the monitoring device 300. The front view 301 faces the monitored environment. The monitoring device 300 includes a camera 302, a fish-eye camera 304, microphone arrays 306A, 306B, infra-red light sensors 308A, 308B, a light sensor 310, a multi-color LED strip 312, a mounting device (i.e., a mount 314), a speaker 316, a control panel 318, and a cover 320 (which may also be referred to as blocking cover). However, a monitoring device according to this disclosure is not so limited and can include fewer, additional, other sensors and/or components, or a combination thereof. While not specifically shown, the monitoring device 300 can also include a processor, as described with respect to the processor 202 of FIG. 2. The monitoring device 300 can also include a memory, such as the memory 204 if FIG. 2.

The camera 302 can be used to view the monitored environment. The camera 302 can include pan, tilt, zoom capabilities so that a remote user, via a user device, such as the user device 106 of FIG. 1, can control the camera 302 to pan, tilt, and/or zoom (PTZ) in order to adjust the view of the monitored environment to a desired view. That is, the monitoring device 300 can receive PTZ commands from the user device. The camera 302 can be capable of a magnification zoom factor of 10×, 12×, 20×, or some other magnification zoom factor. The fish-eye camera 304 can provide a 1800 view of the monitored environment.

The microphone arrays 306A, 306B can be used to capture sounds in the monitored environment. The infra-red light sensors 308A, 308B can be used to improve viewing of the monitored environment, such as the monitoring device 104, under low light conditions, such as at night.

The light sensor 310 can be used to sense the ambient light present in the monitored environment. In an example, the amount of detected ambient light can be used to adjust an intensity of a display that may connected to the monitoring device 300. The multi-color LED strip 312 can be used to give a visual indication to an occupant of the monitored environment of an incoming video and/or audio call, that a video and/or audio call is ongoing, or that a video and/or audio call is not active. The multi-color LED strip 312 can be used to provide other visual indicators to the occupant of the monitored environment.

The mount 314 can be used to mount the monitoring device on top of a monitor or a television. In an example, the monitor can be a portable computing device, such as a tablet. In an example, the monitoring device 300 may not itself include a processor. However, via an external connection (not shown), such as a universal serial bus (USB) connection, a firewire connection, a Bluetooth connection, or the like, can be connected to a general purpose computer to enable the general purpose computer to perform monitoring functions of the monitored environment. As such, by connecting the monitoring device 300 to any processing unit, the processing unit can be turned into a telehealth end point.

In such a configuration, the monitoring device encompasses the processor-less monitoring device plus the processor to which the processor-less monitoring device is connected to.

The speaker 316 can be used to output sounds (e.g., voice, speech, etc.), such as those received from a user device, such as the user device 106 of FIG. 1. The control panel 318 can include controls for muting, unmuting, and controlling the volume of the speaker 316. The control panel 318 can also include controls for controlling whether the camera 302 is enabled or disabled. When the camera 302 is disabled, the camera 302 does not visually (via video or images) capture (e.g., view) the monitored environment.

The cover 320 can be used to block the field of view of the camera 302. The cover 320 is depicted as a dome in FIG. 3, however, the cover 320 may be of another suitable shape. The cover 320 may include a blocking element and the blocking element may be a smart glass. Smart glass, also known as switchable glass, is a type of glass that can be controlled via electrical, thermal, or optical stimuli, to change its light transmission properties. As such, the smart glass may be configured to be at least semi-transparent (i.e., see-through) or opaque (i.e., not transparent). The opacity of the smart glass may be controlled by sending a signal (e.g., an electrical input signal) to the smart glass. For example, the cover 320 may default to an opaque state (i.e., a first state), causing the smart glass to block the field of view of the camera 302. Upon receiving an authenticated request to activate the camera 302, the cover 320 may be configured to become transparent (i.e., a second state) by continuously sending an electrical signal (e.g., a continuous electrical signal) to the cover 320. In some embodiments, such as in the case where the cover is sized to block at least the whole of the camera, the cover 320 can be used to cause the camera 302 to be obscured from view.

Figure 4:
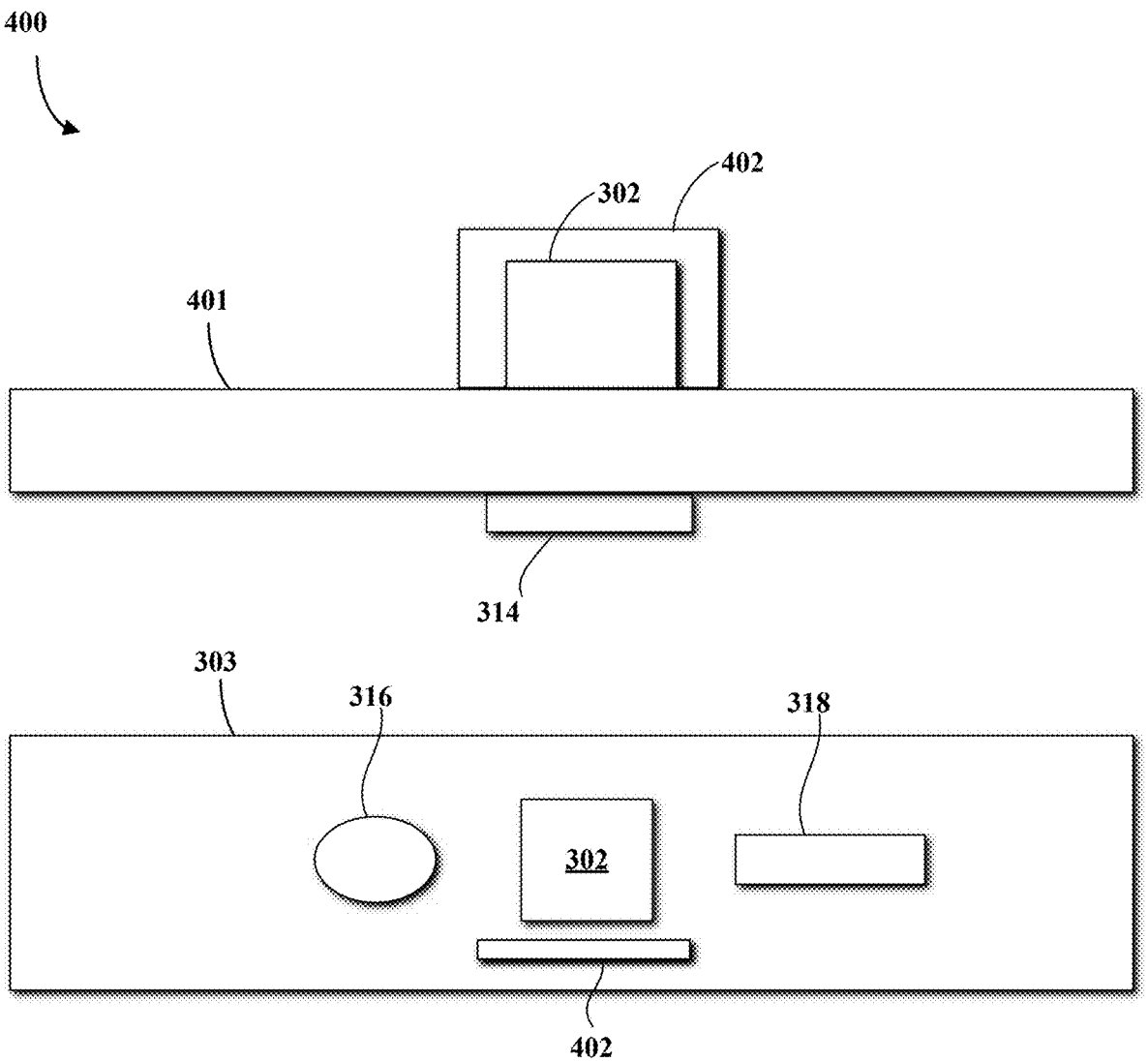
FIG. 4 is a block diagram of an example of a monitoring device according to implementations of this disclosure.

FIG. 4 is a block diagram of an example of a monitoring device 400 according to implementations of this disclosure. The monitoring device 400 can be the monitoring device 104 of FIG. 1. FIG. 4 shows a back view 401 and a top view 303 of the monitoring device 400. The back view 401 faces away from the monitored environment. The monitoring device 400 may be the monitoring device 300 of FIG. 3. The monitoring device 400 includes the camera 302, a mounting device (i.e., a mount 314), the speaker 316 of FIG. 3, the control panel 318 of FIG. 3, and a cover 402. However, a monitoring device according to this disclosure is not so limited and can include fewer, additional, other sensors and/or components, or a combination thereof.

The cover 402 may be attached to the monitoring device 400 such that the cover 402 blocks the field of view of the camera 302 when the cover 402 is in the first state. The cover 402 may be mechanically attached to the monitoring device 400 such that the cover may be controlled to be in the second state so that it does not obstruct the field of view of the camera 302.

The cover 402 is communicatively connected to the monitoring device 400. The monitoring device 400 can transmit signals to the cover 402 to configure the cover 402 to be in different states, including the first state and the second state.

In some implementations, the cover 402 may be a mechanical component (instead of a smart glass) including a blocking element. That is, the cover 402 can be designed as a mechanically actuated shutter (i.e., blocking element), composed of an opaque material that can efficiently obstruct at least the lens of the camera. The cover 402 can be mounted on a linear or rotary actuation system, which can be electronically controlled by a monitoring device 400 via a connected interface. The actuation system enables the shutter (i.e., blocking element) to slide or pivot between two positions: an open position where the camera lens is fully exposed for normal operation, and a closed position where the lens is completely covered, ensuring privacy. The monitoring device 400 can control the movement through software commands, which activate a motor within the actuation system. The motor translates electrical signals into mechanical movement, either directly pushing or pulling the blocking element into place or rotating it out of the camera's field of view.

FIG. 5 is an example of a flowchart of a technique 500 for teleconferencing between a monitoring device and a user device where camera privacy for telemedicine can be used. The technique 500 can be used to establish an audio-visual teleconference between a user of the monitoring device and a user of the user device. When an initial connection is established between the user device and the monitoring device, an audio channel is opened (i.e., enabled, activated, etc.). The video channel is not activated until the remote user of the user device successfully enters a provided entry code.

The technique 500 illustrates one use case of obscuring and unobscuring at least a lens of a camera. However, the disclosure herein is not limited to or by the use case enabled by the technique 500. That is, a cover prevents the camera from viewing anything beyond the cover. In some embodiments the cover may obscure from view the entire camera, such that a person in the same room as the monitoring device would not be able to see the camera while the cover is blocking the field of view of the lens of the camera.

The computing device can be a monitoring device, such as, the monitoring device 104 of FIG. 1, the monitoring device 300 of FIG. 3, or the monitoring device 400 of FIG. 4. The user device can be one of the user devices 106A through 106C of FIG. 1. The technique 500 can be implemented, partially or fully, by the monitoring device. The technique 500 can be implemented, partially or fully, by a server, such as the server 108 of FIG. 1. The technique 500 can be implemented by the computing device, such as the computing device 200 of FIG. 2. The technique 500 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to the processor. Thus, the technique 500 can be implemented, partially or fully, by the processor to which the monitoring device is connected. One or more processors and/or one or more memories may be used.

For example, a hospital room may be equipped with a monitoring device (such as the monitoring device 300 of FIG. 3). A cover (such as the cover 320 of FIG. 3), which may be a smart glass cover, currently obscures the camera lens, ensuring patient privacy. A doctor begins a remote consultation by sending a request to activate the camera located within the room of the patient. This request, however, does not immediately unblock the camera's view. This scenario is referred to herein as door-knocking.

Instead, the system displays a unique authorization code on a display device located with the room of the patient. To proceed, the patient (or assisting hospital staff) provides the doctor with the authorization code. The doctor may then enter the authorization code using a user interface (such as the user interface 800 of FIG. 8). This action may constitute the first condition (e.g., correctly entering the authorization code). Only upon identification of the first condition may the field of view of the lens of the camera be unblocked.

At 502, the technique 500 monitors for a request. The request may be to activate or deactivate the camera located within the room of the patient. The request may arrive via the monitoring device (e.g., monitoring device 104, 300, or 400), a remote server (e.g., server 108), or an associated computing device (e.g., computing device 200). The request may originate from a user device (e.g., user device 106) or may be generated in response to actions within the system itself. The request may include an activation or a deactivation request. The request may include an authorization code.

At 504, the technique 500 receives a first request from a first user device. The first request may be the request being monitored for at 502. The first user device can be a device of a local user (i.e., a local user device) or a device of a remote user (i.e., a remote user device). At 506 the technique 500 determines whether the request is an activation request. That is, the technique 500 determines whether the request is a request to activate the camera (e.g., camera 302 of FIG. 3), which may cause the technique 500 to unblock the field of view of the lens of the camera. If the request is an activation request, the technique continues to 508. If the request is not an activation request, the technique continues to 518.

At 508, the technique 500 determines whether the request originated from a local user (such as a local user device). That is, a determination is made as to whether the activation request is sent by the person receiving a call. If the request did not originate from the local user, the technique continues to 510. If the request did originate from a local user (i.e., a local user device), the technique continues to 514. For example, a hospital room may be equipped with a monitoring device (i.e., the monitoring device 300 of FIG. 3). A doctor may remotely initiate a video consultation with the local user (i.e., the patient). The monitoring device may receive the activation request from the doctor. The monitoring device may analyze the origin of the request and determine that the request did not originate from the local user, but from a remote user device associated with the doctor. Since the request did not originate from the local user (i.e., the patient), the technique proceeds to step 510.

In another example, the monitoring device may receive the activation request from a local user device (i.e., a device associated with the patient). The monitoring device may analyze the origin of the request and determine that the request originated from a user device associated with the patient. Since the request originated from the local user (i.e., the patient), the technique proceeds to step 514.

At step 510, the technique displays an authorization code to a second user device. That is, a unique, dynamically (e.g., randomly) generated, and time-sensitive authorization code is displayed at the second user device. The second user device may be physically located in the room in which the camera associated with the monitoring device (e.g., monitoring devices 104, 300, or 400) is located. The second user device may be a dedicated display, a personal device of a patient (i.e., the local user device), a staff-controlled tablet, or the like.

At 512, the technique 500 receives a second request including the authorization code. The authorization code may be the entry code generated above in reference to 616 of FIG. 6. The authorization code may be received and utilized as previously described.

At 514, the technique 500 identifies a first condition. The first condition may indicate that the monitoring device is to configure the field of view of the lens of the camera to be unblocked. This first condition may be identified in response to receiving the second request including the authorization code. That is, the first condition can be identified in response to the correct entry of the authorization code. Alternatively, the first condition may involve the physical activation of a dedicated camera privacy control (e.g., the control panel 318 of FIG. 3) located within the room. The identification of the first condition does not depend on the field of view of the lens of the camera being blocked.

At 516, the technique 500 configures the cover to be in a second state. That is, the cover is configured such that the cover does not block the field of view of the lens of the camera. Configuring the cover to be in the second state may transition the cover such that the cover no longer obstructs the field of view of the lens of the camera. The cover may be the cover 320 of FIG. 3 or the cover 402 of FIG. 4. The cover may comprise smart glass. As such, the second state corresponds to the smart glass being configured to be at least semi-transparent. This may be achieved by continuously sending an electronic signal (e.g., a continuous electrical signal) from the monitoring device to the cover. Alternatively, the cover may be a mechanical component including a blocking element (i.e., a mechanical cover), as such, the second state might involve retracting or repositioning the blocking element away from the lens of the camera. The change in the state of the cover is triggered by the identification of the first condition, ensuring camera activation aligns with verifiable patient or otherwise authorized consent. After the cover has been configured to be in the first state, the technique 500 may proceed back to operation 502 to monitor for further requests.

At 518, the technique 500 identifies a second condition. The second condition may indicate that the lens of the camera is to be obscured, such as to re-establish privacy.

The second condition may be identified in response to detecting the conclusion of the telemedicine session. To illustrate, the doctor may conclude (e.g., terminate or end) the session using a user interface of the telemedicine software. When the session is concluded, a request is transmitted from the first user device to the monitoring device to terminate the session. The monitoring device may identify the termination request as the second condition.

The second condition may correspond to a patient or an otherwise authorized person physically activating a dedicated camera control (such as the control panel 318 of FIG. 3) or sending a deactivation request through a patient interface. To illustrate, when a friend visits the patient in their hospital room, the monitoring device's camera may make the friend feel uncomfortable. To address this, the patient may press a dedicated camera privacy button to ensure comfort. The camera privacy button may be located on the control panel 318 of FIG. 3, the patient interface, or mounted near the bed of the patient. Pressing the camera privacy button may send a deactivation request to the monitoring device. The monitoring device may recognize the deactivation request as the second condition.

In yet another example, the monitoring device may be present in the room of a patient to monitor the device to monitor the patient for adverse conditions (e.g., monitored conditions) including, but not limited to, fall prevention, bed sore prevention, bed incline monitoring for breathing monitoring, or the like. As such, the camera connected to the monitoring device may be active by default within the patient's room. When the patient receives a visitor, the monitoring device may detect an unknown person within the room. The detection of the unknown person (e.g., the visitor) may trigger the identification of the second condition. As such, the detection of the visitor may indicate that the monitoring device should obscure the lens of the camera.

At 520, the technique 500 configures the cover to be in a first state. The cover being in the first state re-establishes the privacy barrier, blocking the field of view of the lens of the camera. If the cover comprises smart glass, the first state corresponds to the smart glass transitioning back to an opaque state. This may be accomplished by ceasing to send the electronic signal from the monitoring device to the cover. For a mechanical cover, this might involve extending or repositioning the blocking element, as described above in relation to the cover 402 of FIG. 4, to obstruct the field of view of the lens of the camera. The transition to the first state is directly triggered by the monitoring device identifying the second condition. In response, to identifying the second condition, the monitoring device configures the cover to be in the second state. For example, the monitoring device may configure the smart glass dome to being opaque, or the monitoring device configures the mechanical cover to at least obscure the lens of the camera restoring patient privacy. After the cover has been configured to be in the second state, the technique 500 may proceed back to operation 502 to monitor for further requests.

Figure 6:
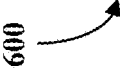
FIG. 6 is an example of an interaction diagram of door-knocking for teleconferencing according to implementations of this disclosure.

FIG. 6 is an example of an interaction diagram 600 of door-knocking (e.g., authorization) for teleconferencing according to implementations of this disclosure. In the interaction diagram 600, a remote user 602, using a user device 606, initiates a teleconference with a local user 604 via the monitoring device 608. The user device 606 can be the user device 106 of FIG. 1 or the computing device 200 of FIG. 2. The monitoring device 608 can be monitoring device 104 of FIG. 1, the computing device 200 of FIG. 2, or the monitoring device 300 of FIG. 3.

At 610, the remote user 602 initiates a teleconference request using the user device 606. In an example, the remote user 602 can initiate the teleconference request using an application, a web page, a link, a user interface, or the like that can be available on the user device 606.

In an example, the teleconference request can be sent directly to the monitoring device to establish a peer-to-peer teleconference session. In another example, the teleconference request can be received at a server (not shown in FIG. 4), such as the server 108 of FIG. 1. The server can manage (e.g., direct, control, issue commands to, monitor, etc.) the monitoring device 608 and can be responsive to requests from the user device 606, as described herein.

Figure 7:
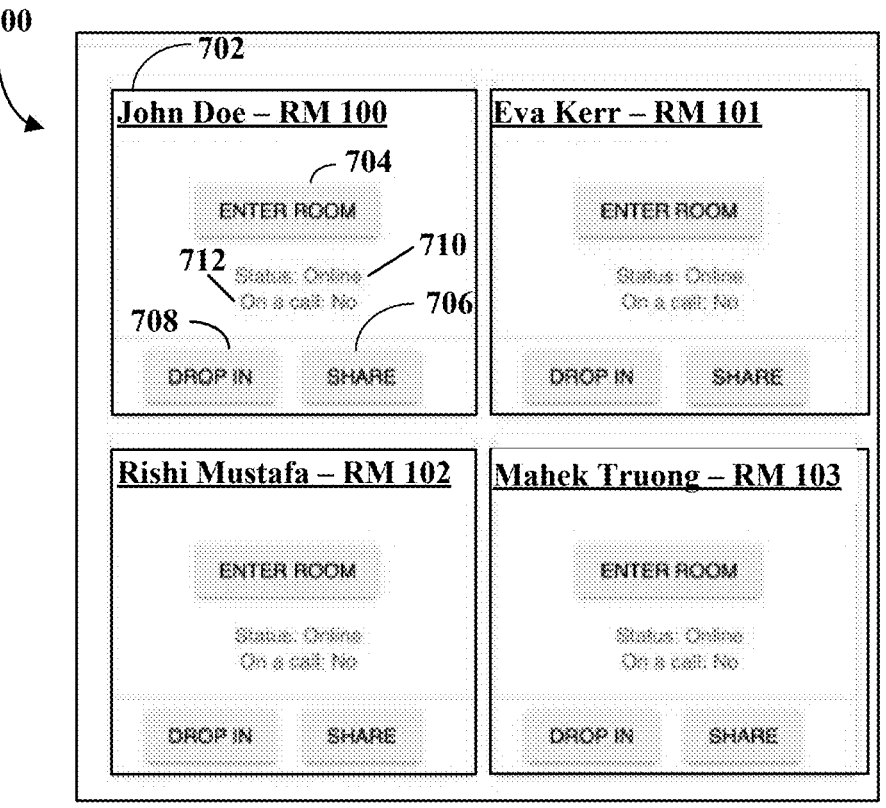
FIG. 7 is an example of a user interface that can be used by a remote user to initiate a teleconference request according to implementations of this disclosure.

FIG. 7 is an example of a user interface 700 that can be used by a remote user to initiate a teleconference request according to implementations of this disclosure. The user interface 700 can be presented on a user device, such as the user device 106 of FIG. 1, of a health care provider, such as a physician. In other implementations, the user interface 700 can include more, fewer, other controls and/or information than those described herein. In other implementations, the user interface 700 can have a different layout than that shown in FIG. 8.

In an example, the user interface 700 can be or can include a listing of all patients who are assigned to the physician. Equivalently, the user interface 700 can include a listing of all the monitoring devices of the patients who are assigned to the physician. For example, the user interface 700 includes an entry 702 that represents the hospital room number 100 of the patient John Doe. The entry 702 includes a control 704 that the physician can use to initiate a teleconference with the monitoring device that is assigned to the patient of the hospital room 100. That a monitoring device is assigned to a patient can mean that the monitoring device is permanently fixed in the room, such as being mounted on a wall of the hospital room; or that the monitoring device is movable and is temporarily placed in the room. For example, the monitoring device may be a robot that can travel from room to room upon the physician requesting to enter a room. For example, the monitoring device can be, or can be mounted on, a telemedicine computer cart that can be transported (e.g., wheeled, pushed, etc.), such as by a nurse, from room to room. In an example, a unique mechanism (e.g., a URL, a web link, or the like) may be associated with a monitoring device. The unique mechanism allows the remote user to initiate a teleconference with the monitoring device.

The entry 702 is shown to also include a share control 706, a drop in control 708, a status 710, and a busy status 712.

Using the share control 706, the remote user can send (e.g., forward, transmit, etc.), or can have sent, to another remote user, information or commands necessary for the other remote user to join an already established teleconference session between the user device 606 and the monitoring device 608. To illustrate, in the course of a telemedicine session, the physician (e.g., the remote user) may need a consult a specialist (e.g., the other remote user). Thus, the physician can share the connection mechanism with the specialist who can use the connection mechanism to join the telemedicine session.

When the remote user activates the drop in control 708, a teleconference session can be established between the user device 606 and the monitoring device 608 where both the audio and the video channels are automatically enabled at the monitoring device 608. That is, when the remote user 602 activates the drop in control 708, an audio and visual teleconference is established and the remote user can hear sounds (e.g., noises, speech, etc.) captured by a microphone of the monitoring device, such as the microphone arrays 306A, 306B of FIG. 3, and see visuals (e.g., video, images, etc.) captured by a camera of the monitoring device, such as the camera 302 of FIG. 3.

In an example, when the remote user activates the drop in control 708, a drop-in request can be received at the server. The server in turn can establish a connection between the user device 606 and the monitoring device 608 and can send commands to the monitoring device to enable the camera, the microphone, and/or speaker of the monitoring device 608. In an example, when the remote user activates the drop in control 708, a drop-in request can be received at the monitoring device 608. The monitoring device 608 can in turn accept the teleconference connection with the user device 606 and enable the camera, the microphone, and/or the speaker of the monitoring device 608.

The status 710 indicates whether the monitoring device of the entry 702 (i.e., of the hospital room 100) is currently accessible (e.g., via a network) from the user device 606. The busy status 712 indicates whether the monitoring device of the entry 702 is currently engaged in another teleconference.

At 612, the teleconference request is sent from the user device 606 to establish a connection with the monitoring device 608. As mentioned above, in an example, the teleconference request can be sent directly to the monitoring device 608 to establish a peer-to-peer teleconference session; and in another example, the teleconference request can be received at the server.

At 613, the audio channel of the teleconference can be established. That is, the speaker(s) of the monitoring device can be enabled so that the local user can hear what the remote user may say. In an example, the server can send a command to the monitoring device 608 to cause the monitoring device 608 to enable the speaker. In an example, a message can alert the local user of the teleconference. For example, a sound (e.g., a chime, etc.) may be output using the speaker(s) of the monitoring device 608. For example, a verbal message such as "incoming teleconference request" may be output. Other auditory or visual messages are also possible. For example, a pre-stored, profile image of the remote user 602 can be displayed to the local user 604. For example, when the remote user 602 initiates the request at 610, an image of the remote user 602 may be captured by a camera of the user device 606 and displayed to the local user 604 on a display of the monitoring device 608.

At 614, the remote user 602 can request that the local user accept the teleconference request. For example, a user interface, such as the user interface of FIG. 9, may be displayed to the remote user 602.

Figure 8:
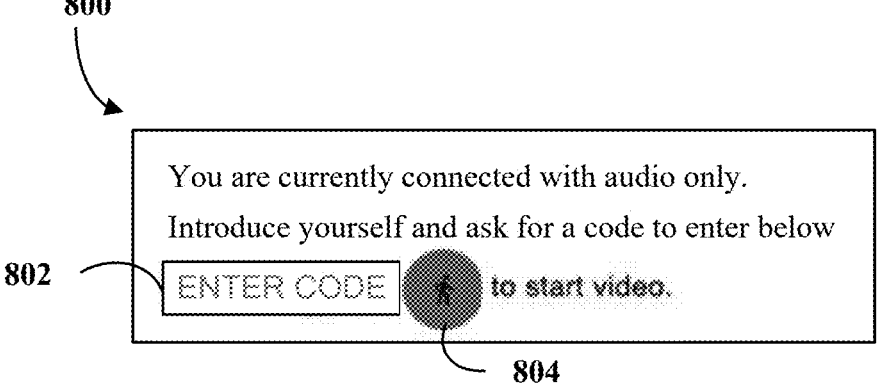
FIG. 8 is an example of a user interface that a remote user can use to request that a local user accept the teleconference request according to implementations of this disclosure.

FIG. 8 is an example of a user interface 800 that the remote user 602 can use to request that the local user 604 accept the teleconference request according to implementations of this disclosure. The user interface 800 can be displayed on the user device 606 of the remote user. The user interface 800 can inform the remote user 602 that an audio-only connection has been established with the monitoring device 608. The user interface 800 can further instruct the remote user 602 to introduce him/herself and request that the local user 604 provide the remote user 602 with an entry code that the remote user 602 enters in a field 802 to start the video channel of the teleconference, after the remote user 602 hits the enter key or presses the control 804.

In an example, the user interface 800 can be overlaid on a blurred static image or a blurred moving image of the monitored environment. In this way, the remote user 602 can tell whether at least someone is in the monitored environment to receive and accept the teleconference request. As mentioned, the view is blurred to protect the privacy of the local user 604. As such, in this example, receiving the blurred image or video from a camera of the monitoring device 608 is not considered that the video channel is enabled.

At 616, the entry code is generated. The entry code can be a string of characters that is randomly generated. The entry code is preferably short, such as three to six characters long. The entry code is preferably numeric. In an example, the server can generate the entry code. In an example, the monitoring device can generate the entry code. The entry code can be displayed on a display of the monitoring device 608. At 618, the local user 604, or another close-by person, can read the entry code to the remote user 602.

In yet another example, the entry code can be obtained from the local user 604. For example, in response to receiving the request for a teleconference from the remote user 602, the local user may be instructed to provide the entry code. In an example, speech recognition can be used to understand an uttered entry code and transmit the speech-recognized entry code to the remote user 602. Text-to-speech can be used at the user device 606 to output the speech-recognized entry code to the remote user 602. In another example, the uttered entry code can be recorded by the monitoring device 608 and the recording of the uttered entry code can be transmitted to the remote user 602 and output via speakers of the user device 606.

In another example, rather than instructing the remote user 602 to request the entry code from the local user 604, the entry code may be electronically sent to the remote user 602. In an example, the server can send the entry code to the remote user 602. In an example, the monitoring device can send the entry code to the remote user 602. In an example, the entry code can be sent to the remote user 602 in a text message to a telephone number of the remote user 602, in an email to an email address of the remote user 602, or the like. In an example, speech recognition can be used to determine whether the local user 604 accepts the teleconference request. For example, in response to a prompt, such as "incoming call from Dr. Jones; Say YES to accept call. Say NO to reject," output by the monitoring device 608, the local user may respond with "yes," "yes, accept call," or the like response indicating acceptance of the teleconference request. In response to the local user 604 indicating acceptance, the entry code can be generated and sent to the remote user 602.

At 620, the remote user 602 enters an entered code in the field 802. The entered code is intended to be the received entry code. However, the remote user 602 may make a mistake in entering the received entry code. In another example, another unauthorized person may be attempting to obtain visual access to the monitored environment by attempting random codes.

At 622, if the entered code matches the received entry code, then the video channel of the teleconference is open. That is, the camera of the monitoring device 608 is enabled. In an example, the server determines whether the entered code matches the received entry code and, if so, issues a command to the monitoring device to enable the camera.

In an example, a validity period can be associated with the entry code. As such, if the entered code is not received, such as at the server or the monitoring device 608, within the validity period, then the teleconference session can be disconnected (e.g., terminated, etc.). That is, the audio channel can be closed and any established network connection between the user device 606 and the monitoring device 608 can be disconnected. The validity period can be 10 seconds, 15 seconds, 20 seconds, fewer, or more seconds.

FIG. 9 is an example of a flowchart of a technique 900 for activating and deactivating camera privacy measures for telemedicine. The technique 900 is usable for obscuring and unobscuring at least a lens of a camera. That is, a cover (e.g., the cover 320 of FIG. 3) is configured to block the camera from viewing anything beyond the cover. In some embodiments the cover may obscure from view the entire camera, such that a person in the same room as the monitoring device would not be able to see the camera while the cover is blocking the field of view of the lens of the camera.

The monitoring device can be the monitoring device 104 of FIG. 1, the monitoring device 300 of FIG. 3, or the monitoring device 400 of FIG. 4. The user device can be the user device 106 of FIG. 1. The technique 900 can be implemented, partially or fully, by the monitoring device. The technique 900 can be implemented, partially or fully, by a server, such as the server 108 of FIG. 1. The technique 900 can be implemented by a computing device, such as the computing device 200 of FIG. 2. The computing device can be the monitoring device. The technique 900 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to the processor. Thus, the technique 900 can be implemented, partially or fully, by the processor to which the monitoring device is connected. One or more processors and/or one or more memories may be used.

At 902, the technique 900 identifies a first condition. The first condition may be identified by the computing device. The first condition may be the same as the first condition described above in relation to 514 of FIG. 5. At 904, the technique 900 transmits a command that causes a cover communicatively connected to the computing device to be in a first state. The command may be transmitted in response to identifying the first condition. The first state may be the same as the first state as described above in relation to 520 of FIG. 5. As such, the first state re-establishes the privacy barrier of the monitoring device. The cover may be the cover 320 of FIG. 3 or the cover 402 of FIG. 4. For example, the cover can be or include a smart glass. For example, the cover can be a mechanical device (i.e., mechanical cover), as described above.

At 906, the technique 900 sends a continuous electrical signal to the cover that causes the cover to be in the second state. The second state may be the second state as described above in relation to 516 of FIG. 5. The continuous electrical signal may be the same as described above in relation to the cover 320 of FIG. 3 or as described above in relation to 516 of FIG. 5.

For simplicity of explanation, the techniques 500 of FIG. 5 and 900 of FIG. 9, are depicted and described as a series of blocks, steps, or operations. However, the blocks, steps, or operations in accordance with this disclosure can occur in various orders and/or concurrently. Additionally, other steps or operations not presented and described herein may be used. Furthermore, not all illustrated steps or operations may be required to implement a technique in accordance with the disclosed subject matter.

While camera privacy for telemedicine is mainly described in the context of a door-knocking scenario, the disclosure herein can be implemented in many condition-based obscuring and unobscuring of a camera lens. Below are presented but a few examples.

In remote work and educational settings, camera privacy becomes critical for maintaining confidentiality and comfort during virtual meetings and classes. This system facilitates a controlled environment where participants can engage visually on an as-needed basis. By enabling users to activate the camera cover automatically through pre-set conditions, such as the start or end of a meeting, privacy concerns are addressed efficiently. This ensures that visual information is shared only during agreed-upon times, enhancing trust and participation in remote engagements.

For security systems requiring intermittent monitoring, such as those in residential or commercial properties, this technology offers a novel approach to camera privacy. By integrating condition-based triggers, such as motion detection or specific time windows, the system can dynamically manage the camera cover's state. This functionality ensures that surveillance is conducted respectfully and in compliance with privacy norms, only capturing footage when predefined conditions are met, thereby balancing security needs with individual privacy rights.

In public spaces or customer service environments, such as banks or retail stores, camera privacy can be managed to protect individuals' privacy while still allowing for necessary surveillance. The system can be programmed to obscure cameras automatically during non-operational hours or when sensitive transactions are occurring. This use case demonstrates the system's versatility in balancing operational needs with privacy concerns, fostering a more privacy-conscious service environment.

In manufacturing settings or sensitive sites where intellectual property protection is crucial, this camera privacy system allows for selective monitoring. The cover can be automatically managed based on specific conditions, such as the presence of authorized personnel or during sensitive processes, to prevent unwanted visual data capture. This targeted approach to privacy enhances security protocols, ensuring that proprietary or sensitive information remains protected.

The disclosure presented herein may be considered in view of the following aspects.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a system. The system includes a computing device. The system also includes a camera that includes a lens. The system also includes a cover extending over at least the lens, where the cover is communicatively connected to the computing device, and the cover is configurable to be in a first state or a second state, the first state configures the cover to block a field of view of the lens to prevent the camera from capturing visual information from a far side of the cover. The computing device is configured to identify a first condition; and in response to identifying the first condition, transmit a signal to the cover that configures the cover to be in the second state. Other embodiments of this aspect include corresponding computer systems, apparatus, and computer programs recorded on one or more computer storage devices, each configured to perform the actions of the methods.

Implementations may include one or more of the following features. The system where the first state causes the camera to be obscured from view and the second state causes the field of view of the lens to be unblocked enabling the camera to capture visual information from the far side of the cover. The computing device can be further configured to, in response to identifying a second condition, transmit a signal to the cover that configures the cover to be in the first state. To identify the second condition may include to receive a first request from a first user device to deactivate the camera. The cover may include a blocking element. The blocking element may include a smart glass and the first state can correspond to the smart glass being opaque and the second state corresponds to the smart glass being at least semi-transparent. The computing device can be further configured to continuously send an electrical signal to the cover that causes the cover to remain in the second state. The computing device can be further configured to cease sending an electrical signal to the cover that configures the cover to be in the first state. The computing device can be further configured to remove the cover from the field of view of the lens that configures the cover to be in the second state. To identify the first condition may include to receive a first request from a first user device to activate the camera; display an authorization code to a second user device; and receive, a second request including the authorization code, from the first user device. Implementations of the described techniques may include hardware, a method or process, or computer software on a computer-accessible medium.

One general aspect includes a method. The method includes identifying a first condition by a computing device; and in response to identifying the first condition, transmitting, by the computing device, a command that causes a cover communicatively connected to the computing device to be in a first state, where the cover extends over at least a lens of a camera, where the cover is configurable to be in the first state or a second state, where the first state configures the cover to block a field of view of the lens from capturing visual information from a far side of the cover. Other embodiments of this aspect include corresponding computer systems, apparatus, and computer programs recorded on one or more computer storage devices, each configured to perform the actions of the methods.

Implementations may include one or more of the following features. The method where the second state may configure the field of view of the lens to be unblocked enabling the camera to capture visual information from the far side of the cover. The cover may include a smart glass. The first state may correspond to the smart glass being opaque and the second state may correspond to the smart glass being at least semi-transparent. The method may include ceasing to send an electrical signal to the cover that configures the cover to be in the first state. The cover may include a blocking element. Implementations of the described techniques may include hardware, a method or process, or computer software on a computer-accessible medium.

One general aspect includes a non-transitory computer readable medium including program instructions that, when executed by a processor of a computing device, cause the processor to perform operations. The operations include identifying a first condition by the computing device; and in response to identifying the first condition, transmitting, by the computing device, a command that causes a cover communicatively connected to the computing device to be in a first state, where the cover extends over at least a lens of a camera, the cover is configurable to be in the first state or a second state, where the first state configures the cover to block a field of view of the lens from capturing visual information from a far side of the cover. Other embodiments of this aspect include corresponding computer systems, apparatus, and computer programs recorded on one or more computer storage devices, each configured to perform the actions of the methods.

Implementations may include one or more of the following features. The operations may include sending an electrical signal to the cover that causes the cover to remain in the second state, where the cover may include a smart glass, the first state corresponds to the smart glass being opaque and the second state corresponds to the smart glass being at least semi-transparent and transitioning the cover from the first state to the second state may include continuously. The operations may include, in response to identifying a second condition, ceasing to send the electrical signal to the cover configuring the cover to be in the first state. The second state may cause the field of view of the lens to be unblocked enabling the camera to capture visual information from the far side of the cover. Implementations of the described techniques may include hardware, a method or process, or computer software on a computer-accessible medium.

The word "example" is used herein to mean serving as an example, instance, or illustration. Any aspect or design described herein as "example" is not necessarily to be construed as being preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise or clearly indicated otherwise by the context, the statement "X includes A or B" is intended to mean any of the natural inclusive permutations thereof. That is, if X includes A; X includes B; or X includes both A and B, then "X includes A or B" is satisfied under any of the foregoing instances. In addition, the articles "a" and "an" as used in this application and the appended claims should generally be construed to mean "one or more," unless specified otherwise or clearly indicated by the context to be directed to a singular form. Moreover, use of the term "an implementation" or the term "one implementation" throughout this disclosure is not intended to mean the same implementation unless described as such.

Implementations of the monitoring device 300, and/or any of the components therein described with respect to FIG. 3 (and the techniques, algorithms, methods, instructions, etc., stored thereon and/or executed thereby) can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

Further, in one aspect, for example, the monitoring device 300 can be implemented using a general purpose computer or general purpose processor with a computer program that, when executed, carries out any of the respective methods, algorithms, and/or instructions described herein. In addition, or alternatively, for example, a special purpose computer/processor can be utilized which can contain other hardware for carrying out any of the methods, algorithms, or instructions described herein.

Further, all or a portion of implementations of this disclosure can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or semiconductor device. Other suitable mediums are also available.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system, comprising:
   a computing device;
   a camera comprising a lens;
   a cover extending over at least the lens, wherein the cover is communicatively connected to the computing device, and the cover is configurable to be in a first state or a second state, the first state configures the cover to block a field of view of the lens to prevent the camera from capturing visual information from a far side of the cover; and
   the computing device, configured to:
      in response to identifying a first condition, transmit a signal to the cover that configures the cover to be in the second state; and
      in response to identifying a presence of an unknown person within an environment monitored by the camera, transmit a signal to the cover that configures the cover to be in the first state.

2. The system of claim 1, wherein the first state causes the camera to be obscured from view.

3. The system of claim 1, wherein the second state causes the field of view of the lens to be unblocked enabling the camera to capture visual information from the far side of the cover.

4. The system of claim 1, wherein the computing device is further configured to:

in response to identifying a second condition, transmit a signal to the cover that configures the cover to be in the first state.

5. The system of claim 1, wherein the cover comprises a blocking element.

6. The system of claim 5, wherein the blocking element comprises a smart glass and the first state corresponds to the smart glass being opaque and the second state corresponds to the smart glass being at least semi-transparent.

7. The system of claim 6, wherein the computing device is further configured to:

continuously send an electrical signal to the cover that causes the cover to remain in the second state.

8. The system of claim 6, wherein the computing device is further configured to:

cease sending an electrical signal to the cover that configures the cover to be in the first state.

9. The system of claim 5, wherein the computing device is further configured to:

remove the cover from the field of view of the lens that configures the cover to be in the second state.

10. The system of claim 1, wherein to identify the first condition comprises to:

receive a first request from a first user device to activate the camera;

display an authorization code to a second user device; and receive, a second request including the authorization code, from the first user device.

11. The system of claim 4, wherein to identify the second condition comprises to:

receive a first request from a first user device to deactivate the camera.

12. A method, comprising:

in response to identifying a first condition by a computing device, transmitting, by the computing device, a first command that causes a cover communicatively connected to the computing device to be in a second state, wherein the cover extends over at least a lens of a camera, wherein the cover is configurable to be in a first state or the second state, wherein the first state configures the cover to block a field of view of the lens from capturing visual information from a far side of the cover; and in response to identifying, by the computing device, a presence of an unknown person within an environment monitored by the camera, transmitting, by the computing device, a second command to the cover that configures the cover to be in the first state.

13. The method of claim 12, wherein the second state configures the field of view of the lens to be unblocked enabling the camera to capture visual information from the far side of the cover.

14. The method of claim 12, the method comprising:

sending a continuous electrical signal to the cover that causes the cover to be in the second state, wherein the cover comprises a smart glass, the first state corresponds to the smart glass being opaque and the second state corresponds to the smart glass being at least semi-transparent.

15. The method of claim 14, the method comprising:

ceasing to send an electrical signal to the cover that configures the cover to be in the first state.

16. The method of claim 12, the method comprising:

removing the cover from the field of view of the lens that configures the cover to be in the second state, wherein the cover comprises a blocking element.

17. A non-transitory computer readable medium including program instructions that, when executed by a processor of a computing device, cause the processor to perform operations, the operations comprising:

in response to identifying a first condition by a computing device, transmitting, by the computing device, a first command that causes a cover communicatively connected to the computing device to be in a second state, wherein the cover extends over at least a lens of a camera, the cover is configurable to be in a first state or the second state, wherein the first state configures the cover to block a field of view of the lens from capturing visual information from a far side of the cover; and in response to identifying, by the computing device, a presence of an unknown person within an environment monitored by the camera, transmitting, by the computing device, a second command to the cover that configures the cover to be in the first state.

18. The non-transitory computer readable medium of claim 17, the operations further comprising:

sending an electrical signal to the cover that causes the cover to remain in the second state, wherein the cover comprises a smart glass, the first state corresponds to the smart glass being opaque and the second state corresponds to the smart glass being at least semi-transparent and transitioning the cover from the first state to the second state comprises continuously.

19. The non-transitory computer readable medium of claim 18, the operations further comprising:

in response to identifying a second condition, ceasing to send the electrical signal to the cover configuring the cover to be in the first state.

20. The non-transitory computer readable medium of claim 17, wherein the second state causes the field of view of the lens to be unblocked enabling the camera to capture visual information from the far side of the cover.

* * * * *